United States Patent [19]
Berg

[11] Patent Number: 5,158,573
[45] Date of Patent: Oct. 27, 1992

[54] INJECTABLE POLYMERIC BODIES

[75] Inventor: Eric P. Berg, Plymouth, Minn.

[73] Assignee: American Medical Systems, Inc., Minnetonka, Minn.

[21] Appl. No.: 675,346

[22] Filed: Mar. 22, 1991

Related U.S. Application Data

[63] Continuation-in-part of Ser. No. 364,722, Jun. 9, 1989, Pat. No. 5,007,940.

[51] Int. Cl.$^5$ ............... A61F 2/02; A61F 2/12; A61M 5/00
[52] U.S. Cl. ................... 623/66; 623/11; 623/8; 424/423
[58] Field of Search ......... 623/66, 11; 604/12, 604/890.1, 891.1, 892.1; 606/86, 92, 76; 424/423

[56] References Cited

U.S. PATENT DOCUMENTS

| | | | |
|---|---|---|---|
| 3,975,350 | 8/1976 | Hudgin et al. | 623/18 |
| 4,631,188 | 12/1986 | Stoy et al. | 424/81 |
| 4,686,962 | 8/1987 | Haber | 604/274 |
| 4,803,075 | 2/1989 | Wallace et al. | 424/423 |

FOREIGN PATENT DOCUMENTS 2227176  7/1990  United Kingdom .

OTHER PUBLICATIONS

Kaufman et al., "Transurethral PTFE Injection" (1984) Journal of Urology vol. 132, pp. 463–464.
Stoy, "New Type of Hydrogel for Controlled Drug Delivery" (1989) Journal of Biomaterials Applications vol. 3, pp. 552–604.

*Primary Examiner*—David Isabella
*Assistant Examiner*—Debra S. Brittingham
*Attorney, Agent, or Firm*—Peter C. Richardson; Lawrence C. Akers; Mark Dryer

[57] ABSTRACT

An injectable composition consisting of a plurality of discrete physiologically-compatible, non-biodegradable, silicone rubber bodies, said bodies having (i) a maximum outside dimension of from about 0.005 to 0.08 inch (125 to 2000μ), (ii) reversible deformability of about 20 to 75% of their unstressed outside dimension and (iii) a lubricious surface, wherein the lubricious surface is provided by a thin film coating of a liquid lubricant; and a method for treating a tissue condition in a patient using said composition.

9 Claims, No Drawings

INJECTABLE POLYMERIC BODIES

This is a continuation-in-part of patent application Ser. No. 364,722, filed Jun. 9, 1989, now U.S. Pat. No. 5,007,940.

BACKGROUND OF THE INVENTION

This invention relates to an injectable composition consisting of physiologically-compatible bodies, particularly those made of deformable silicone rubber. The composition of the invention is adapted to be used in a method for treating a tissue condition, particularly for tissue augmentation, by injecting said composition into the site of said condition, as described and claimed in application Ser. No. 364,722 (U.S. Pat. No. 5,007,940).

The use of various injectable or inflatable polymeric bodies for tissue augmentation and prosthetic implants is known in the art. For example, U.S. Pat. No. 4,686,962 discloses an assembly for hypodermically implanting a genitourinary prosthesis for the treatment of urinary incontinence which includes an inflatable containment membrane which is inflated by material injected with a hypodermic needle.

Urinary incontinence also has been treated by the transurethral injection of polytetrafluoroethylene (PTFE), usually in the form of a paste or encapsulated particles. See, for example, "Transurethral Polytetrafluoroethylene Injection for Post-prostatectomy Urinary Incontinence" by M. Kaufman et al, the *Journal of Urology*, Vol. 132, Sep. 1984, p. 463–464, and the references cited therein. However, if the particles are small, complications arise from undesirable migration or removal by phagocytes causing potential problematical accumulation at other sites, for example the brain, kidney or lungs.

U.S. Pat. No. 4,803,075 discloses an injectable implant composition for soft tissue augmentation comprising an aqueous suspension of a particulate biomaterial, preferably fibrillar cross-linked collagen, and an amount of a biocompatible fluid lubricant.

Another application for tissue augmentation is in the treatment of a hypoplastic breast wherein a typical prior art prosthesis is provided by a silicone membrane enveloping a suitable bulking material, for example a saline solution or a flexible polysiloxane gel. One disadvantage of the saline-containing prosthesis is that microleaks in the silicone membrane or valving mechanism lead to deflation of the prosthesis. A problem with polysiloxane gel is that it contains low-molecular weight compounds, such as cyclic oligomers, which slowly migrate into the patient's system and cause problems similar to those associated with the PTFE particles discussed above.

A solution to the problems associated with earlier polymeric implants is provided by U.S. Pat. No. 4,631,188, which discloses a method of in situ formation of a solid polymer in a mammal which comprises injecting into said mammal a physiologically-acceptable polymeric composition comprising a solution in a water-soluble, non-toxic polar solvent of a water-insoluble, non-toxic, non-cross-linked polymer or copolymer selected from polymers and copolymers of acrylonitrile or vinylacetate, linear or slightly branched polymers and copolymers of 2-hydroxyethylacetate and methacrylate, poly-(N-vinyliminocarbonyl), polycondensates and polyadducts and having a solubility parameter of from about 9.2 to about 15.5 $(cal/cc)^{\frac{1}{2}}$.

The water-insoluble non-toxic polymers used in the method disclosed in U.S. Pat. No. 4,631,188 fall within the class of compounds known in the art as water-swellable hydrogels and the disclosure in said patent relating to this class of compounds is incorporated herein by reference. As noted in the patent, water-swellable hydrogels have been used in the art for tissue augmentation, usually in implants of defined shape and size. The method disclosed in the patent overcomes problems associated with such preformed implants by injecting a solution of said hydrogel into a mammal resulting in the in situ formation of a solid polymer in the mammal. This method involves the use of a water-soluble polar solvent, for example dimethyl sulfoxide (DMSO), which, although non-toxic, is an unnecessary adjunct to the implant and has to be dispersed by the mammal's metabolism. Furthermore, since the polymer is water-insoluble but water-swellable, formation of the solid polymer is dependent upon the amount of water present in the mammalian tissue and the size and shape of the implant is difficult to control.

U.S. Pat. No. 5,007,940 discloses and claims an injectable composition consisting of a plurality of discrete physiologically-compatible, non-biodegradable, polymeric bodies, said bodies having (i) an average outside diameter of from about 0.005 to 0.20 inch, (ii) reversible deformability of about 20 to 75% of their unstressed outside diameter, and (iii) a lubricious surface.

The preferred injectable composition of U.S. Pat. No. 5,007,940 is based upon a water-insoluble, non-toxic hydrogel which does not contain undesirable solvents. Moreover, the discrete, deformable bodies, since they already contain their full complement of water, retain their individual identity and are stable after injection so that the size and shape of the implant does not alter.

It has now been found that an alternative material which may be used for the discrete, deformable polymeric bodies is medical grade silicone rubber.

However, although this silicone material possesses the desired characteristics for the stated injectable composition it does not have the optimum lubricious surface. Accordingly, to make it suitable for use in an injectable composition the particles thereof are coated with a thin film of a liquid lubricant. As used herein the term thin film means just sufficient lubricant to coat the surface of the silicone rubber bodies without forming a separate liquid phase. It is to be understood that the resultant composition is not a dispersion, suspension or paste but a composition of discrete, deformable bodies having the same physical characteristics as the composition disclosed in U.S. Pat. No. 5,007,940.

SUMMARY OF THE INVENTION

In accordance with the present invention there is provided an injectable composition consisting of a plurality of discrete physiologically-compatible, non-biodegradable, silicone rubber bodies having (i) a maximum outside dimension of about 0.005 to 0.08 inch (125 to 200μ), (ii) reversible deformability of about 20 to 75% of their unstressed outside dimension, and (iii) a lubricious surface, wherein the lubricious surface is provided by a thin film coating of a liquid lubricant. Preferably the silicone rubber bodies have a particle size range from about 0.007 to 0.045 inch.

The injectable composition of the invention preferably is prepared by cryogenically grinding medical grade silicone rubber using liquid nitrogen to provide a silicone aggregate, screening the aggregate to obtain bodies of the desired particle size and coating the bodies with an appropriate liquid lubricant to provide the desired lubricious surface.

A preferred liquid lubricant for the composition of the invention is a solution of 5% polyvinyl pyrrolidone (PVP) in glycerol. Particularly preferred is PVP having a molecular weight of about 360,000.

Another preferred liquid lubricant is 0.2% hyaluronic acid of molecular weight about 600,000 in a glycerol/water mixture, wherein the major proportion is glycerol, preferably 90:10 glycerol/water.

Other suitable liquid lubricants include solutions of: (a) 10% dextran in glycerol; (b) 50% dextran in phosphate buffered saline; (c) 25% PVP in phosphate buffered saline; and (d) 2.0% hyaluronic acid in phosphate buffered saline.

It is to be noted that hyaluronic acid having a molecular weight of the order of 600,000 is soluble in a glycerol/water mixture, preferably 90:10 glycerol/water. Hyaluronic acid having a higher molecular weight, for example 1,500,000, is not soluble in 90:10 glycerol/water, but forms a gel in such a mixture.

The injectable composition of the invention suitably may be used for treating a tissue condition in a patient by injecting into the tissue site a tissue enhancing amount of the composition.

DETAILED DESCRIPTION OF THE INVENTION

The injectable composition of the invention comprises discrete bodies of a particular size and possessing unique characteristics which enable them to be injectable, i.e. to be introduced into and contained within a hypodermic needle, without the aid of a carrier or solvent. Thus, the injectable composition is not a traditional solution, suspension, dispersion or paste, but consists of a plurality of the above-described discrete bodies themselves. The injectability of the bodies is particularly surprising because in many instances the average size of the bodies is greater than the inside diameter of the needle in which they are to be used. Thus, as more particularly described hereinafter, when the bodies are somewhat elongated and irregular in shape, the average outside diameter of the bodies may be greater than the inside diameter of a hypodermic needle through which they may be successfully passed without undergoing observable damage.

The unique and surprising injectability of the discrete bodies which form the composition of the invention may be attributed primarily to the characteristics which are defined herein as reversible deformability and lubricious surface.

As used herein the term "reversible deformability" means that the bodies are sufficiently flexible to be deformed into virtually any shape by folding, compression or both when subjected to the physical stress required to produce the relevant deformation, for example the deformation required to introduce the bodies into a hypodermic needle, but return to their original shape and size when said stress is removed, e.g. when they are expressed from the needle.

It is also essential that each discrete body has a lubricious surface, i.e. said surface must be sufficiently smooth and slippery so that the bodies do not stick to any surface with which they come into contact during the performance of the invention, for example, the inside surface of a hypodermic needle, nor do they stick to themselves. The fact that the bodies do not stick to themselves means that they slip with respect to each other and, when injected, can be contoured or manipulated into any desired shape and subsequently retain their discrete identity and do not form undesirable lumps or agglomerates.

The lubricity of the bodies is provided by coating the surface of the bodies with a thin film of a liquid lubricant. Suitable liquid lubricants include solutions of (i) polyvinyl pyrrolidone in glycerol or phosphate buffered saline; (ii) hyaluronic acid in a glycerol/water mixture or phosphate buffered saline; or (iii) a water-soluble polysaccharide, such as dextran, in glycerol or phosphate buffered saline.

The discrete silicone rubber bodies present in the composition of the invention have a maximum outside dimension of from about 0.005 to 0.08 inch; preferably about 0.007 to 0.045 inch. Thus they are large enough to avoid undesirable migration from the site of injection, which was serious problem with the microparticles, for example PTFE, used in the prior art. However, because of the deformability characteristic described hereinabove, they are still small enough to be injectable without undergoing irreversible damage.

In a particularly preferred embodiment of the invention the silicone rubber bodies are somewhat elongated and irregular in shape and have a maximum outside dimension of from about 0.007 to 0.045 inch. Bodies having an average dimension at the upper end of the stated range may be injected through a 19ga needle (internal diameter 0.032 inch) with no apparent damage.

The following Example illustrates a preferred process for preparation of the unique discrete, deformable and slippery bodies which provide the injectable composition of the invention.

EXAMPLE

Medical grade silicone rubber (Dow Corning 4735) is cryogenically ground using liquid nitrogen to provide a silicone aggregate of a screened particle size distribution from about 0.007 to 0.045 inch (175 to 1125$\mu$). This material is then added at 50% w/w to a solution of 5% polyvinyl pyrrolidone (PVP) (M. W. about 360,000) in glycerol. After degassing to remove air bubbles, the resulting composition consisting of discrete, deformable bodies coated with a thin film of the liquid lubricant, is placed into a 1 cc syringe fitted with a 19ga thin-walled 1½" needle having an internal diameter of 0.032 inch.

The composition was capable of being injected into subcutaneous tissue sites in guinea pigs using unassisted thumb pressure.

The above procedure was repeated with similar results with the following liquid lubricants:

10% Dextran in glycerol;
50% Dextran in phosphate buffered saline;
25% PVP in phosphate buffered saline;
0.2% hyaluronic acid (M. W. about 600,000) in 90:10 glycerol/water; and
2.0% hyaluronic acid in phosphate buffered saline.

Instead of being placed in a syringe and used immediately, the bodies prepared as described above may be recovered and may be stored in a suitable sterile non-solvent liquid, for example, saline solution.

The injectable composition of the invention is particularly suitable for the treatment of a number of tissue conditions in mammals, particularly humans. The expression "tissue conditions" as used herein is intended to be generic to any situation or condition which requires augmentation, enhancement, medication, strengthening or replacement of tissue, and includes, but is not limited to: tissue augmentation of a hypoplastic breast; transurethral and periurethral injection to treat urinary incontinence; tissue augmentation of scar tissue; and treatment of tissue deficiency arising from severe wounds, e.g. "plastic surgery".

The aforesaid tissue conditions may be treated by injecting into the tissue site a tissue enhancing amount of an injectable composition according to the invention.

The composition preferably is injected into the tissue through a hypodermic needle of about 25ga to 14ga. The gauge of the needle used will depend upon the size (outside diameter) of the bodies in the composition. Thus, when the bodies are somewhat elongated and irregular in shape having an average outside dimension of about 0.007 to 0.045 inch they will pass through a needle of 19ga (about 0.032 inch internal diameter) with no apparent damage.

In a preferred application of the composition of the invention, urinary incontinence may be treated by a method which comprises urethral tissue augmentation by injecting the above described injectable composition into the patient's urethra.

I claim:

1. An injectable composition consisting of a plurality of discrete physiologically-compatible, non-biodegradable, silicone rubber bodies, said bodies having (i) a maximum outside dimension of from about 0.005 to 0.08 inch (125 to 2000μ), (ii) reversible deformability of about 20 to 75% of their unstressed outside dimension, and (iii) a lubricious surface, wherein the lubricious surface is provided by a thin film coating of a liquid lubricant.

2. A composition according to claim 1, in which said silicone rubber bodies have a maximum outside dimension of from about 0.007 to 0.045 inch (175 to 1125μ).

3. A composition according to claim 2, in which said liquid lubricant is a solution of 25% polyvinyl pyrrolidone having a molecular weight of about 360,000 in phosphate buffered saline.

4. A composition according to claim 1, in which said liquid lubricant is selected from the group consisting of (i) a solution of polyvinyl pyrrolidine in glycerol or phosphate buffered saline; (ii) a solution of hyaluronic acid in a glycerol/water mixture or phosphate buffered saline; and (iii) a solution of a water-soluble polysaccharide in glycerol or phosphate buffered saline.

5. A composition according to claim 4, in which said liquid lubricant is a solution of 5% polyvinyl pyrrolidone having a molecular weight of about 360,000 in glycerol.

6. A composition according to claim 4, in which said liquid lubricant is a solution of 0.2% hyaluronic acid having a molecular weight of about 600,000 in 90:10 glycerol/water.

7. A composition according to claim 4, in which said liquid lubricant is a solution of 2.0% hyaluronic acid in phophate buffered saline.

8. A composition according to claim 4, in which said liquid lubricant is a solution of 10% dextran in glycerol.

9. A composition according to claim 4, in which said liquid lubricant is a solution of 50% dextran in phosphate buffered saline.

* * * * *